US009670137B2

(12) United States Patent
Ferguson

(10) Patent No.: US 9,670,137 B2
(45) Date of Patent: Jun. 6, 2017

(54) USING NOVEL AMINES TO STABILIZE QUATERNARY TRIALKYLALKANOLAMINES

(71) Applicant: Huntsman Petrochemical LLC, The Woodlands, TX (US)

(72) Inventor: Dave C Ferguson, Spring, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 0 days.

(21) Appl. No.: 14/347,781

(22) PCT Filed: Apr. 8, 2013

(86) PCT No.: PCT/US2013/035575
§ 371 (c)(1),
(2) Date: Mar. 27, 2014

(87) PCT Pub. No.: WO2013/154968
PCT Pub. Date: Oct. 17, 2013

(65) Prior Publication Data
US 2015/0028253 A1 Jan. 29, 2015

Related U.S. Application Data

(60) Provisional application No. 61/623,958, filed on Apr. 13, 2012.

(51) Int. Cl.
*C07C 213/10* (2006.01)
*A01N 25/22* (2006.01)
(Continued)

(52) U.S. Cl.
CPC ............ *C07C 213/10* (2013.01); *A01N 25/22* (2013.01); *A01N 25/32* (2013.01); *C07C 213/04* (2013.01)

(58) Field of Classification Search
None
See application file for complete search history.

(56) References Cited

U.S. PATENT DOCUMENTS 4,464,461 A  8/1984  Guild
5,209,858 A  5/1993  Heinsohn et al.
(Continued)

FOREIGN PATENT DOCUMENTS

EP  0 364 895 A1  4/1990
JP  52014708 A  2/1977
(Continued)

OTHER PUBLICATIONS

JP Office Action dated Jan. 11, 2017 in corresponding application (JP 2015-505822); Translation of reasons for rejection.

*Primary Examiner* — Joseph D Anthony
(74) *Attorney, Agent, or Firm* — Huntsman International LLC

(57) ABSTRACT

New stabilizers for solutions of choline hydroxide and related quaternary trialkylalkanolamines are disclosed. The stabilizers are alkyl hydroxylamines, hydrazines, hydrazides, or derivates thereof, including compounds containing more than one such functionality. The new stabilizers are effective at concentrations less than about 1000 ppm, and choline hydroxide solutions stabilized with the compounds described herein typically have Gardner Color change less than about 2.0 after six months at reasonable temperatures.

6 Claims, 1 Drawing Sheet

(51) Int. Cl.
*A01N 25/32* (2006.01)
*C07C 213/04* (2006.01)

(56) References Cited

U.S. PATENT DOCUMENTS

| | | | |
|---|---|---|---|
| 8,163,951 B2 | 4/2012 | Szarvas et al. | |
| 9,216,944 B2 * | 12/2015 | Moonen | C07C 213/04 |
| 2003/0170342 A1 | 9/2003 | Raczek et al. | |
| 2005/0014667 A1 * | 1/2005 | Aoyama | C11D 7/08 510/175 |
| 2005/0272842 A1 | 12/2005 | Alford et al. | |
| 2007/0135321 A1 | 6/2007 | Patel et al. | |
| 2007/0193708 A1 | 8/2007 | Broucek et al. | |
| 2009/0099051 A1 * | 4/2009 | Aoyama | C11D 7/08 510/176 |
| 2009/0165978 A1 | 7/2009 | Hagiopol et al. | |
| 2011/0118165 A1 * | 5/2011 | Lee | G03F 7/426 510/176 |
| 2011/0247650 A1 * | 10/2011 | Lee | C11D 1/22 134/3 |
| 2014/0329184 A1 * | 11/2014 | Moonen | C07C 213/10 430/331 |
| 2014/0361217 A1 * | 12/2014 | Moonen | C07C 213/10 252/182.29 |
| 2015/0031917 A1 | 1/2015 | Moonen et al. | |

FOREIGN PATENT DOCUMENTS

| | | | |
|---|---|---|---|
| JP | 59-134752 | * | 8/1984 |
| JP | S59 134752 A | | 8/1984 |
| JP | S63 63643 A | | 3/1988 |
| JP | 2002-317193 A | | 10/2002 |
| JP | 2003-267937 A | | 9/2003 |
| JP | 2004-067548 A | | 3/2004 |
| JP | 2004067548 A | | 3/2004 |
| JP | 2008-500982 A | | 1/2008 |
| JP | 2015501798 A | | 1/2015 |
| WO | 03/064581 A1 | | 8/2003 |
| WO | 2013/076190 A1 | | 5/2013 |
| WO | 2013/077855 A1 | | 5/2013 |
| WO | 2013/098575 A1 | | 7/2013 |

* cited by examiner

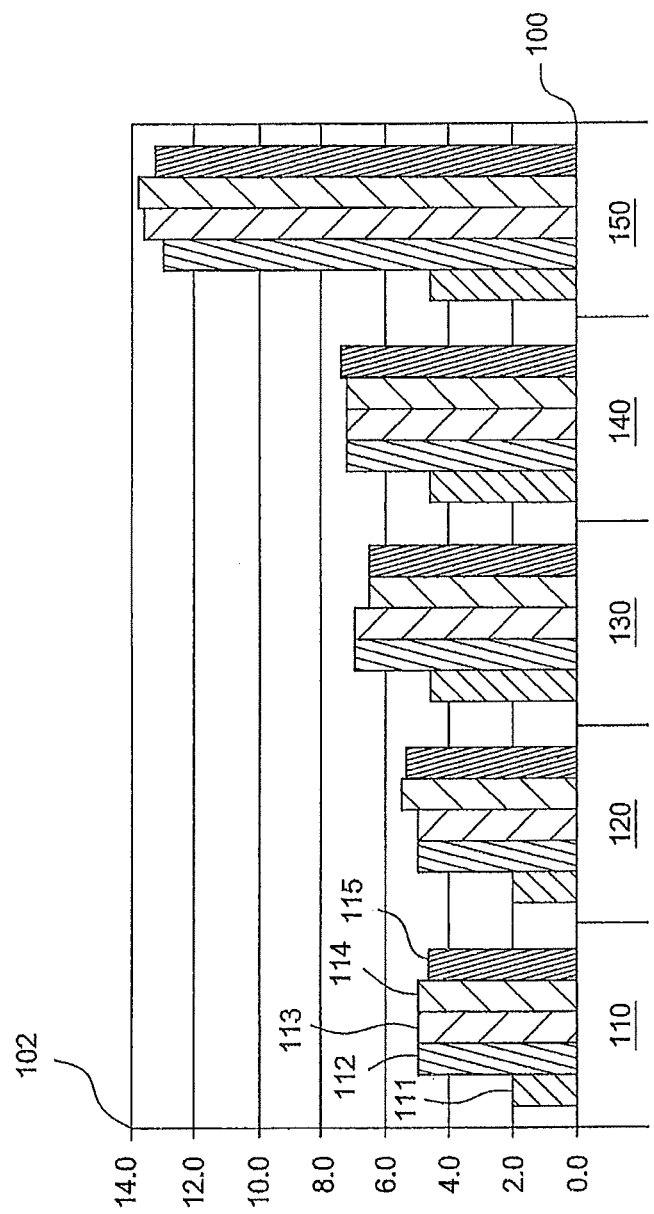

USING NOVEL AMINES TO STABILIZE QUATERNARY TRIALKYLALKANOLAMINES

CROSS REFERENCE TO RELATED APPLICATIONS

This application is the U.S. National Phase of International Application PCT/US2013/035575, filed Apr. 8, 2013, which designated the U.S., and which claims priority to U.S. Provisional App. Ser. No. 61/623,958 filed Apr. 13, 2012. The noted applications are incorporated herein by reference.

BACKGROUND OF THE INVENTION

Field of the Invention

Embodiments described herein generally relate to choline hydroxide compositions, variants thereof, and methods of preparing such compositions. Specifically, embodiments described herein relate to stabilizers for such compositions and methods of stabilizing such compositions.

Description of the Related Art

Choline hydroxide (trimethylhydroxylamine), and variant quaternary trialkylalkanolamines thereof, are used in the agricultural chemical industry as neutralizing agents for herbicidal active ingredients such as 2,4-dicholorophenoxyacetic acid (2,4-D-acid), 3,6-dichloro-2-methoxybenzoic (dicamba) acid, and N-phosphonomethylglycine (glyphosate). Products such as 2,4-D choline, dicamba choline, and glyphosate choline provide convenient forms for handling and distributing the component herbicides. Choline hydroxide may also be neutralized with hydrochloric acid to make choline chloride, which is used as animal feed. Choline hydroxide is also used in some semiconductor applications as a caustic component of electroless plating solutions or as a photoresist stripping reagent.

Choline hydroxide is made by reacting aqueous trimethylamine with ethylene oxide at a maximum temperature of 45° C. Variants are made by similar reactions involving different amines and alkylene oxides. If not stabilized, choline hydroxide decomposes to its volatile components and their adducts over time. Trimethylamine is a strong colorant and carries a strong odor of fish oil, making it easily detectable in a choline hydroxide mixture. Acetaldehyde may be produced by decomposition of choline hydroxide, and may oxidize or polymerize over time to paraldehyde. These decomposition products of choline hydroxide and its variants impart color to insufficiently stabilized solutions.

Sodium borohydride and lithium aluminum hydride, and their alkali metal variants, have historically been used as stabilizers for choline hydroxide in applications for which the presence of alkali metals is tolerated. In other applications, hydroxylamine salts such as hydroxylamine acetate and hydroxylamine sulfate may be used at relatively high levels such as 0.2 wt % or more. Formaldehyde and paraformaldehyde have been shown to stabilize choline hydroxide for applications tolerant of organic solvents. Sodium bisulfate, sodium metabisulfite, sodium sulfite, sodium thiosulfate, ammonium bisulfite, and ammonium bisulfate provide reasonable stabilization at low concentration levels, but decline in activity after 4 weeks at 40° C. Amines such as monoethanolamine (MEA), diethanolamine (DEA), triethanolamine (TEA), dimethylaminopropylamine (DMAPA), isopropylamine (IPA), aminoethoxyethylamine (AEEA), and trimethylamine (TMA) have been found to work to varying degrees at high concentrations. However, solutions stabilized with TMA at concentrations from 0.2 wt % to 5 wt % turn black after one week at 40° C. Thus, there is still a need for a method of stabilizing choline hydroxide and its variants for long periods of time using low stabilizer levels for agricultural applications.

SUMMARY OF THE INVENTION

Embodiments described herein include a quaternary trialkylalkanolamine composition, which may be a choline hydroxide solution, comprising a stabilizer from the group consisting of an alkyl hydroxylamine, a hydrazide, a hydrazine, and a mixture thereof. The stabilizer may be used at concentrations below about 1000 ppm, and the stabilized solution typically has a Gardner Color change less than about 2.0 after six months.

Other embodiments described herein include a method of stabilizing a quaternary trialkylalkanolamine solution, the method comprising providing a liquid stabilizer comprising a dialkylhydroxylamine, a hydrazide, a hydrazine, or a derivative thereof, and blending the liquid stabilizer with the solution to form a stabilized solution. The liquid stabilizer may be diethylhydroxylamine (DEHA), hydrazine, and/or carbodihydrazide, or derivatives thereof.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The inventors have discovered new ways to stabilize aqueous choline hydroxide solutions, and variants thereof, using nitrogen compounds. Choline hydroxide may be formed by reacting aqueous trimethylamine with ethylene oxide.

Choline hydroxide is a quaternary ethanolamine compound, derivatives of which may be formed by using amine precursors other than trimethylamine. Use of alkylene oxides other than ethylene oxide may also yield variant quaternary trialkylalkanolamines. Exemplary variants that may be stabilized according to the methods and compositions herein include, but are not limited to, trimethylpropanolamine, triethylethanolamine, dimethylethylethanolamine, diethylmethylethanolamine, dimethylethylpropanolamine, diethylmethylpropanolamine, triethylpropanolamine. In general, a quaternary trialkylalkanolamine that may benefit from the methods and compositions described herein has the formula $[R^1R^2R^3NR^4OH]^+[OH]^-$, wherein $R^1$, $R^2$, $R^3$, and $R^4$ is each a lower alkyl group such as methyl, ethyl, or propyl. Choline hydroxide is a molecule according to the above formula where $R^1$, $R^2$, and $R^3$ is each a methyl group and $R^4$ is an ethyl group. For purposes of explanation, the following discussion describes methods and compositions for stabilizing choline hydroxide solutions, but such methods and compositions are also applicable to the foregoing variants and other related, but not named, variants.

Choline hydroxide solutions in water tend to develop color, and precipitate solids, over time. It is believed that choline hydroxide decomposes mainly into its constituents, trimethylamine and ethylene glycol, but that small amounts of acetaldehyde are also formed as the bonding electrons between carbon and nitrogen migrate along the axis of the carbon chain to form a carbon oxygen double bond rather than cross directly to the oxygen atom. It is believed that acetaldehyde imparts color to the solution over time, and may polymerize to varying degrees to form solids. Trimethylamine may also impart color to the solution over time.

Aldehyde scavenger compounds can be used to prevent the acetaldehyde from polymerizing and reduce coloration by reacting with the acetaldehyde to form a non-chromophore before the acetaldehyde can polymerize. In general, amine derivatives may react as nucleophiles with aldehydes to form imines, oximes, enamines, and the like. Hydroxylamines, in particular, react with aldehydes to form oximes. Hydrazine and derivatives thereof may similarly react with aldehydes to form hydrazones. Compounds having higher nucleophilic strength will typically be better aldehyde scavengers, and will stabilize a choline hydroxide solution at lower usage levels. For example, a solution of about 45 wt % choline hydroxide is effectively stabilized by diethylhydroxylamine (DEHA) at a concentration of about 500 ppm, and by carbohydrazide (also known as carbodihydrazide) at a concentration as low as 250 ppm. In one example, a choline hydroxide solution stabilized with 250 ppm carbodihydrazide has Gardner Color change less than about 2.0 after 6 months shelf life at nominal temperatures. Solutions that have higher concentrations of stabilizer, or that use more effective stabilizers, may show Gardner Color change less than 1.5 or less than 1.0 after 6 months at nominal temperatures.

Effective stabilizers for choline hydroxide solutions must themselves be stable in a high pH environment. Citric acid, which is otherwise an excellent stabilizer, reacts with choline hydroxide to form a salt. It is theorized that the sodium sulfites have limited utility for this reason. It is also theorized that ammonium bisulfite and ammonium bisulfate have better utility than sodium sulfites for this reason. Generally, stabilizers useful for choline hydroxide must be able to withstand a pH of 12-14 without hydrolyzing.

A composition comprising a quaternary trialkylalkanolamine in a water-containing solvent at a concentration between about 0.1 wt % and about 80 wt % may be stabilized using an alkyl hydroxylamine, a hydrazide, a hydrazine, or a mixture thereof. In general, alkyl hydroxylamines, hydrazines, and hydrazides are effective to stabilize strong aqueous choline hydroxide solutions at levels below about 0.2 wt % stabilizer based on total weight of the solution. Choline hydroxide is commonly used in 45% aqueous solutions that are very basic, having pH generally between 12 and 14. Such conditions favor strong nucleophilic attack on aldehydes to make derivative compounds that do not impart color. The more effective stabilizers will stabilize an aqueous 45% choline hydroxide solution at concentrations of 1000 ppm or less, for example 750 ppm stabilizer concentration. The most effective stabilizers are effective at concentrations of 500 ppm or less, for example at 300 ppm or 250 ppm.

The alkyl groups of the alkyl hydroxylamine stabilizer may be any alkyl group that does not overly hinder the nucleophilic nitrogen atom or substantially reduce the nucleophilicity of the unpaired nitrogen electrons, which form the basis of amine nucleophilicity. Mono- or dialkyl hydroxylamines are both effective, but dialkyl hydroxylamines are generally more effective as stabilizers. The alkyl groups may be the same, as in DEHA, or different, and may be linear, branched, or cyclic. In some cases, one or more conjugated alkyl groups may be used, if desired, including aromatic groups. Alkyl groups such as methyl, ethyl, propyl, isopropyl, butyl, and isobutyl are examples of alkyl groups that may appear in alkyl hydroxylamines usable as choline hydroxide stabilizers.

Hydrazine, substituted hydrazines and hydrazides may also be used effectively as stabilizers for solutions of choline hydroxide and it variants, reacting with acetaldehyde decomposition products to produce hydrazones. Hydrazine itself is effective, although hydrazine is often difficult to use. Molecules having dual or multiple functionality, such as hydroxylamines having hydrazine or hydrazide derived substituents or hydrazines/hydrazides with hydroxylamino substiuents, for example a compound having the general formula

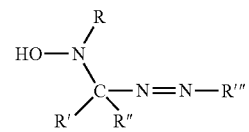

where R, R', R", and R'" each independently represents hydrogen or any desired alkyl group, including carbonyl groups, may also be used as a stabilizer for choline hydroxide solutions or their derivatives. Such stabilizers are essentially grafted mixtures of the hydroxylamine, hydrazine, and/or hydrazide stabilizers described above.

Variants of choline hydroxide in which one or more of the methyl groups is replaced by an oxygen or nitrogen containing functiional group may also benefit, to varying degrees, from the stabilization described herein. If the functional group is an oxygen or nitrogen containing group, propensity for forming acetaldehyde or other chromophores by decomposition is expected to decline because the electron density around the hydroxyl oxygen is reduced by the shift in overall electron density toward the additional electronegative functional groups. Such compounds would be expected to require less stabilizer. If the functional group contains aromaticity, delocalization of electrons around the aromatic center will also improve stability for similar reasons. Under sufficiently hydrolyzing conditions, however, such compounds may nonetheless benefit from similar stabilization.

The stabilizers described herein may be added to a choline hydroxide, or variant, solution as a solid or a liquid, and may be dissolved in water or another solvent miscible with water prior to mixing with the choline hydroxide solution. For example, DEHA is a liquid at room temperature and is commonly used as an 85% solution in water. Such a solution may be mixed with a 45% choline hydroxide solution in water to form a stabilized choline hydroxide solution. The mixing may be performed in-line, for example using an in-line or static mixer, as the choline hydroxide solution is formed, or the stabilizer may be mixed in a mixing tank or a transporation vehicle or package, such as a bottle, tank, truck, or railcar.

While choline hydroxide is normally used as an aqueous solution, other solvents may be used to carry choline hydroxide along with the stabilizers described herein. Polar solvents such as alcohols, for example methanol, ethers, sulfoxides, and the like may be used. Carbonyl-containing solvents are typically not used with the stabilizers described herein, because solvents that may react with the stabilizer are avoided. In some cases, the choline hydroxide, or other quaternary trialkylalkanolamine, forming reaction may be performed in the presence of a non-aqueous polar solvent, and the stabilizer added afterward. Further, a stabilizer may be blended into the reaction mixture before the quaternary trialkylalkanolamine is formed. In other embodiments, a variant of choline hydroxide may be formed by reacting a hydroxylamine such as DEHA with ethylene oxide, or another alkylene oxide, and excess DEHA may be used to stabilize the resulting compound.

FIG. 1 is a graph showing the choline hydroxide stabilizing performance of DEHA and carbodihydrazide in a number of examples. The data show the evolution of Gardner Color in a 45% aqueous choline hydroxide solution maintained in an oven at 40° C. at various durations. Axis 100 shows the examples as 110, 120, 130, 140, and 150. Axis 102 is Gardner Color index. Each bar of an example represents a different duration in the oven. Each bar 111 is the initial Gardner Color (i.e. color after zero days). Each bar 112 is Gardner Color after 5 days. Each bar 113 is Gardner Color after 15 days. Each bar 114 is Gardner Color after 25 days. Each bar 115 is Gardner Color after 40 days.

Each of the examples 110, 120, 130, 140, and 150 was prepared from a stock aqueous 45% choline hydroxide solution made from an aqueous solution of trimethylamine and ethylene oxide. Example 110 was prepared by putting 100 g of the stock solution into a glass vessel equipped with suitable stopper and adding 1000 ppm by weight of DEHA. Example 120 was prepared by putting 100 g of the stock solution into a glass vessel equipped with suitable stopper and adding 500 ppm by weight of DEHA. Example 130 was prepared by putting 100 g of the stock solution into a glass vessel equipped with suitable stopper and adding 500 ppm by weight of carbodihydrazide. Example 140 was prepared by putting 100 g of the stock solution into a glass vessel equipped with suitable stopper and adding 250 ppm by weight of carbodihydrazide. Finally, example 150 was prepared by putting 100 g of the stock solution into a glass vessel equipped with a suitable stopper without adding a stabilizer. Example 150 thus serves as a reference.

The data of FIG. 1 show Gardner Color growth of the stabilized examples 110, 120, 130, and 140 generally half that of the unstabilized example 150, or less. Examples 110 and 120 showed generally similar performance. Examples 130 and 140 showed higher color growth than examples 110 and 120, but still evidence effective stabilization of the overall solution. The data also show that the stabilized solutions generally exhibited Gardner Color growth less than about 2.0 over the 40 day test period, while the unstabilized solution showed Gardner Color growth of approximately 4.0 over the same period at the same conditions.

It should be noted that a stabilized quaternary trialkylalkanolamine composition may be used in any convenient form. Besides a direct aqueous solution, the composition may be emulsified or otherwise dispersed in an immsicible medium, if desired, or used as a dispersion medium to carry an immiscible or insoluble material that is not reactive with any component of the composition.

While the foregoing is directed to embodiments of the present invention, other and further embodiments of the invention may be devised without departing from the basic scope thereof, and the scope thereof is determined by the claims that follow.

The invention claimed is:

1. A composition comprising a quaternary trialkylalkanolamine and a stabilizer selected from the group consisting of a hydrazide with a hydroxylamino substituent, a hydrazine with a hydroxylamino substituent and a mixture thereof.

2. The composition of claim 1, wherein the quaternary trialkylalkanolamine is choline hydroxide.

3. The composition of claim 1, wherein the stabilizer is hydrazine with a hydroxylamino substituent.

4. The composition of claim 1, wherein the concentration of the stabilizer in the composition is not more than about 500 ppm.

5. The composition of claim 1, wherein the concentration of the stabilizer in the composition is not more than about 300 ppm.

6. The composition of claim 1, wherein the composition has a Gardner Color change less than about 2.0 after 6 months.

* * * * *